United States Patent [19]

Cells

[11] Patent Number: 4,824,611
[45] Date of Patent: * Apr. 25, 1989

[54] PREPARATION OF HYDROCARBON-SOLUBLE TRANSITION METAL SALTS OF ORGANIC CARBOXYLIC ACIDS

[75] Inventor: Paul L. Cells, Cleveland, Ohio

[73] Assignee: Mooney Chemicals, Inc., Cleveland, Ohio

[*] Notice: The portion of the term of this patent subsequent to Dec. 30, 2003 has been disclaimed.

[21] Appl. No.: 800,458

[22] Filed: Nov. 21, 1985

Related U.S. Application Data

[63] Continuation-in-part of Ser. No. 682,925, Dec. 18, 1984, abandoned.

[51] Int. Cl.$^4$ .................. C11C 1/00; C07F 9/00; C07F 11/00; C07F 13/00
[52] U.S. Cl. ................... 260/414; 556/44; 556/49; 556/55; 556/61; 556/114; 556/149
[58] Field of Search .............. 260/414; 556/44, 49, 556/61, 149, 114, 55

[56] References Cited

U.S. PATENT DOCUMENTS

| | | | |
|---|---|---|---|
| 3,076,830 | 2/1963 | Conn | 260/429 R |
| 3,256,266 | 6/1966 | Burt | 260/414 X |
| 3,297,586 | 1/1967 | Duck et al. | 260/429 R |
| 3,362,972 | 1/1968 | Kollar | 260/414 |
| 3,595,891 | 7/1971 | Cavitt | 260/429 R |
| 3,689,515 | 9/1972 | Smith | 260/429 R |
| 4,374,777 | 2/1983 | Henry et al. | 260/414 |
| 4,633,001 | 12/1986 | Cells | 556/44 |

Primary Examiner—Paul F. Shaver
Attorney, Agent, or Firm—Renner, Otto, Boisselle & Sklar

[57] ABSTRACT

A process for preparing hydrocarbon-soluble transition metal salts of organic carboxylic acids having improved properties wherein the transition metal is one capable of having a multiplicity of oxidation states is described. The process comprises the steps of (a) providing at least one transition metal compound wherein the transition metal is at one of its higher positive oxidation states, (b) treating said transition metal compound with at least one inorganic reducing agent forming an intermediate containing the transition metal in a lower positive oxidation state, and (c) reacting said intermediate with at least one organic carboxylic acid containing at least 5 carbon atoms to form the transition metal salt of said carboxylic acid. The transition metal salts prepared in accordance with the process of the invention are useful in a variety of applications including resins, inks, paints, lubricants and fuels.

17 Claims, No Drawings

PREPARATION OF HYDROCARBON-SOLUBLE TRANSITION METAL SALTS OF ORGANIC CARBOXYLIC ACIDS

CROSS-REFERENCE TO RELATED APPLICATION

This application is a continuation in-part of my copending Application Ser. No. 682,925, filed Dec. 18, 1984, now abandoned, the specification and claims of which are hereby incorporated by reference.

BACKGROUND OF THE INVENTION

This invention relates to an improved method of preparing transition metal salts of organic carboxylic acids having improved stability and shelf life and wherein the transition metal is one capable of having a multiplicity of oxidation states. The invention also relates to the transition metals salt composition prepared in accordance with this procedure and to the use of said transition metal salts and a variety of applications including resins, inks, paints, lubricants and fuels.

Metal salt compositions, including transition metal salt compositions have been described in the prior art as being useful in a variety of applications including: siccatives for paints, varnishes and inks; stabilizers in diverse plastics; curing agents in polyesters; additives for grease and lubricating oils; and additives for fuels and fuel oils.

It is well known that metal soaps serve in a wide variety of specific industrial uses to catalyze the transformation of drying oils into solid condition by promoting the mechanism of oxidation, polymerization and association. Lead, cobalt, manganese and calcium soaps are among those commonly employed for this purpose.

Many types and mixtures of metal salts and soaps of natural or synthetic organic acids, particularly carboxylic acids, have been suggested and commercially offered for several decades. One of the advantages of metal salts and soaps of carboxylic acids is that they provide a source of metals in forms which are soluble in organic liquids, especially in various hydrocarbon oils and solvents, to form solutions having various desired properties and uses. The desire for economy in the production of such materials or for improved product quality has led to a number of variations and methods of producing the metal soap compounds. Moreover, as various organic carboxylic acids have become available in commercial quantities, either from new natural sources, or as synthetic acids or standardized synthetic acid mixtures, the possibility of using these acids to produce metallic salts or soaps has been motivated, for example, by a lower price; by a relative uniformity of the commercial acids; by better color; or at times the non-colored characteristics of the salt products; by higher solubility of the salt products and various solvents; or improved stability in storage of the metal compositions or of their solutions.

Methods of preparing hydrocarbon soluble salts of molybdenum and vanadium have been described in the literature. In U.S. Pat. No. 3,362,972, the process for preparing the salts of molybdenum and vanadium is described which comprises heating an oxalate compound of a metal of the group consisting of molybdenum at a valence of +6 and a vanadium at a valence of +5 with a hydrocarbon carboxylic acid of from 4 to 50 carbon atoms. The oxalate compound is prepared by heating oxalic acid with molybdenum or vanadium oxide in about equimolar amounts in the presence of water at a temperature of from about 100°-150° C. In U.S. Pat. No. 3,578,690, a procedure is described which does not require the use of oxalic acid. In the 690 patent, the process comprises the direct reaction of a molybdenum compound with a carboxylic acid at an elevated temperature while removing the water from the reaction mixture. A critical feature of this process is the removal of free water during the reaction, and generally, of about 100°-300° C. are utilized. In order temperatures to facilitate the removal of water, solvents such as lower alkyl benzenes and alkanes are included in the reaction mixture, and the water is removed azeotropically. Polish Pat. No. 89551 also describes a method of obtaining organic salts of molybdenum and vanadium. The method described in the Polish patent involves heating a mixture of molybdenum trioxide or vanadium pentoxide, an aliphatic alcohol containing from 2 to 8 carbon atoms, concentrated hydrochloric acid having a density of 1.179 at 20, a carboxylic acid in the form of a fatty or naphthenic acid, and alkyl benzene as a solvent. The mixture is heated at the boiling point of the mixture while continuously removing water from the mixture. After the reaction is completed, excess solvent is removed. It is reported that the mixture of aliphatic alcohol and hydrochloric acid functions as a reducing agent.

U.S. Pat. No. 3,076,830 describes and claims the preparation of water-soluble vanadium (IV) salts having as an anion, a complex of an oxo-vanadium group with an organic acid residue derived from an organic complexing acid such as glycollic, salicyclic and tartaric acids. The procedure comprises heating an aqueous medium containing a lower aliphatic carboxylic acid of 2 to 4 carbon atoms, a reducing compound such as hydrazine, and ammonium metavanadate until the evolution of nitrogen has essentially ceased, and thereafter adding a base consisting of hydroxides and carbonates of alkali metal and ammonium cations, and the organic complexing acid as defined above. The water-soluble salt then is isolated. The patentees teach (Col. 4, lines 51–54) that the vanadyl compounds prepared in the first step are useful also in the preparation of other vanadyl compounds.

SUMMARY OF THE DISCLOSURE

This invention relates to hydrocarbon-soluble transition metal salt compositions of organic carboxylic acids having improved stability and shelf life. More particularly, the invention relates to the process for preparing hydrocarbon-soluble transition metal salts of organic carboxylic acids, the salts thus prepared, and their use in various applications including resin formulations, inks, paints, lubricants and fuels. The present invention is applicable to transition metals which are capable of having a multiplicity of oxidation states, and the process for preparing the salts comprises the steps of (a) providing at least one transition metal oxide compound wherein the transition metal is at one of its higher positive oxidation states, (b) treating (reducing) said transition metal oxide compound with at least one inorganic reducing agent forming an intermediate containing the transition metal in a lower positive oxidation state, (c) reacting said intermediate with at least one alicyclic carboxylic acid containing at least 5 carbon atoms to form the transition metal salt of said carboxylic acid.

DESCRIPTION OF THE PREFERRED EMBODIMENTS

In general, the present invention relates to a process of preparing transition metal salts from transition metals which are capable of having a multiplicity of oxidation states. In the process of the present invention, the first step comprises providing a transition metal compound (preferably an oxide) wherein the transition metal is at one of its higher positive oxidation states. The transition metal is one from the first transitional series, and of the transitional elements found in the first transitional series, namely, scandium, titanium, vanadium, chromium, manganese, iron, cobalt and nickel, vanadium, molybdenum, tungsten and rhenium are preferred. Vanadium and molybdenum are especially preferred transition metals for use in the present invention. The transition metals utilized in the present invention are normally used in the form of the transition metal oxide compounds. Specific examples of useful transition metal oxide compounds include vanadium pentoxide, ammonium metavanadate, molybdenum trioxide, ammonium molybdate (VI), tungsten trioxide, ammonium tungstate, etc.

In the second step of the process of the present invention, the transition metal oxide compound is treated with at least one inorganic reducing agent to form an intermediate containing the transition metal in a lower positive oxidation state. Any inorganic reducing agent which is capable of reducing a transition metal in its higher positive oxidation state to a lower positive oxidation state may be utilized in the process of the present invention. Examples of such reducing agents include metal bisulfites such as sodium bisulfite and various hydrazine sources. The hydrazine source used in the present invention is a compound or mixture of compounds which is capable of producing hydrazine under the conditions of the reaction in sufficient quantity to reduce the transition metal oxide from a higher to a lower positive oxidation state. Many such hydrazine sources are known to those of skill in the art. See, for example, the book entitled "Hydrazine" by Charles C. published by the Mathieson Chemical Corporation of Clark, Baltimore, M.D. (1953), particularly pages 31 through 71 and 120 through 124; and the book entitled "The Chemistry of Hydrazine" by L.F. Audrieth and B.A. Ogg, published by John Wiley and Son, New York (1951), especially pages 209 through 223. The hydrazine sources are the preferred reducing agents.

Among the more common, and therefore preferred hydrazine sources, are hydrazine itself, hydrazine hydrate and solutions of hydrazine and water, as well as hydrazinium salts of, for example, sulfuric and hydrochloric acid, semicarbazides and thiosemicarbazides and their analogous salts; hydrazine dicarboxylates of lower alkanols (e.g., ROOCNHNHCOOR) and their dimers as well as the amino guanidines and their —NHNH—sulfuric and hydrochloric acid salts and benzene sulfonyl hydrazides and their bisoxy analogs. Mixtures of hydrazine sources can also be used. This list is not intended to be exhaustive or in any way limit the invention and many useful hydrazine sources similar to those listed will occur to those skilled in the art.

For reasons of economy and ease of handling, hydrazine and particularly its solutions with water and other solvent/diluents are preferred. A typical hydrazine source is a mixture of water and hydrazine containing about 64% hydrazine, although similar mixtures containing more or less hydrazine (about 20–80%; more often, about 30–70% hydrazine) can be used.

Techniques of using such hydrazine sources in chemical reactions are well known to those of skill in the art, as for example is shown by the books cited above and the article entitled "Hydrazine" in Kirk-Othmer Encyclopedia of Chemical Technology, Second Edition, Vol. 11, pages 164–196, Interscience Publishers, New York, New York (1966). These are hereby incorporated by reference for their relevant disclosures in regard to techniques for using hydrazine sources.

The organic carboxylic acids which are utilized in the process of the present invention for preparing transition metal salts generally contain from about 5 and more generally from about 6 to about 30 carbon atoms and are preferably aliphatic or alicyclic monocarboxylic acids. In one embodiment the monocarboxylic acids are aliphatic or alicyclic monocarboxylic acids containing 8 to 10 carbon atoms. Mixtures of two or more monocarboxylic acids can be and generally are utilized in the preparation of the salts of the present invention. In addition to mixtures of acids containing 5 or more carbon atoms, mixtures of monocarboxylic acid containing 2 to 4 carbon atoms with acids containing more than 5 carbon atoms can be used. In these latter mixtures, the amount of the higher molecular weight acid in the mixture should be sufficient to render the transition metal salt soluble in hydrocarbons. The carboxylic acids or acid mixtures may be natural in origin or derived from a natural product, or the acid or acid mixture may be composed of synthetic acids. Mixtures of natural and synthetic acids also can be utilized. Examples of useful acids and acid mixtures which contain from 5 to 30 carbon atoms include acetic isopentanoic acid, hexoic acid, 2-ethyl butyric acid, 2-ethylhexanoic acid, isooctanoic acid, isononanoic acid, commercially available standardized nonanoic acid, decanoic acid neodecanoic acid, oleic acid, stearic acid, naphthenic acid, tall oil acid, palmitic acid, lauric acid and other natural and synthetic acids and acid mixtures. Examples of other useful mixtures includes, for example, mixtures of propionic acid and 2-ethyl hexanoic acid; oxalic acid and 2-ethylhexanoic acid; etc.

The reaction of the intermediate containing the transition metal in a lower positive oxidation state with at least one organic carboxylic acid (step (c)) to form the metal salt of the said carboxylic acid may be, and preferably is conducted, in the presence of a promoter which is generally at least one nitrogen-containing compound. The nitrogen-containing compound generally may be ammonia, ammonium compounds such as ammonium hydroxides, and ammonium halides, or organic nitrogen compounds or mixtures thereof. Ammonia generally is added as ammonium hydroxide or an ammonium halide such as ammonium chloride. Although only a small amount of ammonia generally is used, the reaction may be facilitated by the incremental addition of ammonia during the heating step. Similarly only a small amount of organic amine is needed to be effective to initiate and promote the reaction, and the reaction is promoted further by the addition of ammonia during the heating step.

The organic amines useful as promoters in the invention can be aliphatic or aromatic amines and polyamines. The aliphatic amines may be alkyl amines such as n-hexylamine and n-octyl amine, or substituted aliphatic amines such as alkanolamines. Polyamines and poly-alkanolamines also are useful as well as heterocyclic amines including pyridene, picoline, etc.

Aliphatic amines containing from about 10 to 30 carbon atoms, and mixtures of aliphatic amines are useful. For example, two commercially available aliphatic amine mixtures are Primene 81R which is a mixture of $C_{12}$ and $C_{14}$ aliphatic amines, and Primene JM-T which is a mixture of $C_{18}$ and $C_{20}$ aliphatic amines. Both of these materials are available under these trade designations from Rohm and Haas Co. Among the aromatic amines found to be useful is ortho-phenetidene and N,N'-substituted p-phenylene diamines such as those having the formula

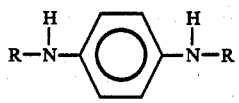

wherein each R is independently an alkyl group containing up to 10 carbon atoms. One example of such a compound is Santoflex 77 available from Monsanto Co. wherein each R group is a 1,4-dimethylpentyl group.

The reaction mixture generally contains a non-reactive hydrocarbon diluent which preferably is mineral spirits, mineral oil, synthetic oil or mixtures thereof. The mineral spirits generally utilized have a boiling range of about 149° to about 205° C.

The reaction mixture also may contain other materials for various ancillary purposes, for example, to serve as dispersing agents, viscosity modifiers, etc. Examples of viscosity modifiers which are useful in the process of the invention include materials such as glycols, alcohol ethers, or glycol ethers, amines, phosphate ester, etc. Some of the ancillary constituents may react and combine with the metal, but the net effect is not deleterious to the process or the ultimate product. For example, alkoxy alkanols of higher molecular weight and boiling ranges may be left in the final product either as a combined organic moiety or merely as a mixture.

Glycols or polyols and glycol ethers often are included as ancillary materials, particularly as viscosity modifiers, and these materials generally fall within the formula

[$R_n(OR')_yOH$]$_z$          (I)

wherein
R is hydrogen or an alkyl group having from 1 to about 10 carbon atoms,
n is 0 or 1,
R' is an alkylene group having 2, 3 or 4 carbon atoms which may be substituted with hydroxyl groups,
y is an integer from 0 to 4, and
z is a value of 2 when n is 0, and a value of 1 when n is 1.

The amount of the glycols, polyols or glycol ethers incorporated into the reaction mixture is not critical and can be varied depending on properties desired for the reaction mixture.

Examples of glycols or polyols and glycol ethers represented by the above Formula I include Cellosolve (2-ethoxyethanol); methyl Cellosolve (2-methoxyethanol); Carbitol (diethylene glycol monoethylether); butyl Cellosolve (2-butoxyethanol); diethylene glycol, triethylene glycol, dipropylene glycol, tripropylene glycol, polypropylene glycol, tetraethylene glycol, ethylene glycol and Sorbitol. Mixtures of glycols and glycol ethers can also be used.

Examples of phosphate esters which can be utilized as viscosity modifiers, etc. in the reaction mixture include alkyl and aryl phosphates and acid phosphates. Examples of such esters include tributyl phosphate, triamyl phosphate, triphenyl phosphate, tricresyl phosphate, mono amyl acid phosphate, mono butyl acid phosphate, diamyl acid phosphate, dibutyl acid phosphate, and mixtures of one or more of said esters.

The amount of reducing agent utilized in step (b) is that amount which is effective in reducing the transition metal of the transition metal oxide compound to a lower positive oxidation state. Generally, the amount of reducing agent should be sufficient to reduce substantially all of the transition metal from its higher positive oxidation state to a lower positive oxidation state. Accordingly, the mole ratio of transition metal oxide compound provided in step (a) to inorganic reducing agent incorporated into step (b) will be from about 1:0.1 to about 1:5. The reduction of the transition metal from its higher oxidation state to a lower oxidation state occurs at room temperature although the rate of reduction appears to be increased with increasing temperature. Accordingly, the reduction step (b) generally will be conducted at a temperature of from about room temperature up to about 85° C. Higher temperatures may be utilized, but appear to offer no advantage.

The intermediate which is obtained in step (b) and which contains the transition metal in a lower positive oxidation state is reacted with at least one organic carboxylic acid to form the desired transition metal salt. The amount of organic carboxylic acid utilized in step (c) may vary over a wide range although it is generally desired that the equivalent ratio of transition metal to organic carboxylic acid be at least about 0.5:1 and more generally will be at least about 1:1. The reaction between the transition metal intermediate and the organic carboxylic acid can occur at room temperature although the rate of the reaction appears to be increased with increasing temperature. Accordingly, the reaction of step (c) generally is conducted at a temperature of from about room temperature up to about 200° C.

Elevated pressures can be utilized in steps (b) and (c) of the process of the present invention, but these steps generally are conducted at about atmospheric pressure.

Although the process of this invention for preparing the transition metal salts is described herein as a sequence of steps (a), (b) and (c), it is not necessary that the reactants be added to the reaction mixture sequentially. As illustrated in some of the examples below, a mixture containing the transition metal compound, the reducing agent and the organic carboxylic acid can be prepared and heated to an elevated temperature. The initial reaction is the desired reduction described as step (b) followed by reaction of the transition metal in its lower valence state with the organic carboxylic acid present in the mixture.

The transition metal salts prepared in accordance with the method of this invention are hydrocarbon soluble and water-insoluble. Generally, the transition metal salts prepared by the process of the invention are green in color.

The following examples illustrate the process of the present invention for preparing the transition metal salts. Unless otherwise indicated in the following examples and elsewhere in the specification and appended claims, all parts and percentages are by weight, and all temperatures are in degrees centigrade.

EXAMPLE 1

A mixture of 410 parts of mineral spirits, 115 parts of hydrazine hydrate, and 100 parts of ammonium metavanadate is prepared, and 100 parts of distilled water are added to improve the dispersion. The mixture is heated to a temperature of about 70° C. over a period of about 40 minutes whereupon 44 parts of 2-ethylhexanoic acid are added over a period of about 4 minutes. The mixture is heated to a temperature of about 95° C., and 40 parts of propionic acid are added. After heating the mixture to a temperature of 90°-100° C. for one hour, the mixture is thereafter cooled and filtered through a filter aid. The filtrate is the desired product which is green in color.

EXAMPLE 2

A mixture of 57 parts of butyl Cellosolve, 360 parts of mineral spirits, 80 parts of ammonium metavanadate, 420 parts of 2-ethylhexanoic acid, 40 parts of propionic acid and 40 parts of water is prepared and heated to 30° C. whereupon 5 parts of oxalic acid are added. After heating this mixture to about 85° C., 115 parts of hydrazine hydrate are added, and after 25 minutes of stirring, an additional 100 parts of mineral spirits are added. The mixture is heated to about 140° C. for about one hour, cooled and filtered. The filtrate is the desired green vanadium salt.

EXAMPLE 3

A mixture of 57 parts of butyl Cellosolve, 410 parts of mineral spirits and 100 parts of ammonium metavanadate is prepared at about 20° C., and 115 parts of hydrazine hydrate are added as the temperature reaches 25° C. The mixture is sparged with nitrogen and heated to about 80° C. whereupon 52 parts of valeric acid and 368 parts of 2-ethylhexanoic acid are added. This mixture then is heated to about 140° C. over a period of about 1.5 hours and filtered through a filter aid. The filtrate is the desired product which is green in color.

EXAMPLE 4

A mixture of 57 parts of butyl Cellosolve, 390 parts mineral spirits and 100 parts of ammonium metavanadate is prepared and heated to about 70° C. Hydrazine hydrate (120 parts) is added as the temperature of the reaction mixture is increased to 80° C. Valeric acid (52 parts) and 518 parts of 2-ethylhexanoic acid are added with stirring. The mixture is heated to 150° C. and an additional 20 parts of valeric acid are added. After stirring an additional 30 minutes, the mixture is filtered through a filter aid, and the filtrate is the desired product which is green in color.

EXAMPLE 5

A mixture of 100 parts of tributyl phosphate, 200 parts of mineral spirits, 90 parts of ammonium metavanadate, 600 parts of 2-ethylhexanoic acid, 40 parts of propionic acid and 40 parts of pelargonic acid is prepared, and 100 parts of hydrazine hydrate are added. This mixture is sparged with nitrogen and heated to 80° C. over a period of about one hour and filtered. The filtrate is the desired product which is green in color.

EXAMPLE 6

A mixture of 100 parts of tributyl phosphate, 200 parts of mineral spirits, 93.5 parts of ammonium metavanadate, 600 parts of 2-ethylhexanoic acid, 40 parts of propionic acid and 40 parts of pelargonic acid is prepared, and 100 parts of hydrazine hydrate are added with stirring. The reaction mixture reaches a temperature of about 40° C. over a period of 2.5 hours. Heat is applied to raise the reaction temperature to 98° C., and an additional 30 parts of hydrazine hydrate are added. When the reaction temperature reaches 155° C., the heat is removed and the reaction mixture is cooled and filtered. The filtrate is the desired product which is green in color.

EXAMPLE 7

A mixture of 200 parts of ammonium metavanadate, 600 parts of mineral spirits and 200 parts of hydrazine is prepared and heated to 55° C. whereupon 900 parts of 2-ethylhexanoic acid are added. The reaction temperature is raised to 105° C. over a period of about 2.5 hours. After cooling overnight, the mixture is reheated to a temperature of about 85° C. and sparged with carbon dioxide as the mixture is heated to about 150° C. Neodecanoic acid (300 parts) is added and the mixture is maintained at this temperature for an additional 15 minutes. The mixture is filtered, and the filtrate is the desired product which is green in color.

EXAMPLE 8

A mixture of 239 parts of ammonium heptamolybdate (51.58% molybdenum) and 500 parts of mineral spirits is prepared, and 300 parts of hydrazine hydrate are added at room temperature. The reaction is exothermic to about 33° C. 2-ethylhexanoic acid (800 parts) is added, and the reaction is exothermic to 55° C. After cooling the mixture to about 45° C., 200 parts of isononanoic acid are added and the temperature is increased to 150° C. over a period of about 5.5 hours. After cooling overnight, the mixture is heated to 38° C. and sparged with air for about 45 minutes while heating the mixture to about 150° C. The mixture is filtered, and the filtrate is the desired product which is green in color.

EXAMPLE 9

A mixture of 239 parts of ammonium heptamolybdate (51.58% molybdenum), 800 parts of isonanoic acid and 500 parts of mineral spirits is prepared and heated to about 150° C. in two hours. After cooling overnight, the mixture again is heated to 150° C. and maintained at this temperature for 1.5 hours, and an additional 239 parts of ammonium heptamolybdate are added followed by 25 parts of hydrazine hydrate. After stirring for an additional 1.5 hours at about 150° C., an additional 55 parts of hydrazine hydrate are added over a period of one hour while maintaining the reaction temperature at between about 125°-150° C. Propionic acid (40 parts) is added followed by 30 parts of hydrazine hydrate at a temperature of about 150° C. The mixture then is cooled and filtered. The filtrate is the desired product.

The hydrocarbon-soluble transition metal salts prepared in accordance with the invention are useful in a variety of applications including lubricants, fuels, resins inks and paints.

The transition metal salts of the invention can be effectively employed in a variety of lubricating compositions formulated for a variety of uses. These lubricating compositions are based on diverse oils of lubricating viscosity, including natural and synthetic lubricating oils and mixtures thereof. These lubricating compositions containing the subject additive are effective as crankcase lubricating oils for spark-ignited and compression-ignited internal combustion engines, including automobile and truck engines, two-cycle engines, aviation piston engines, marine and low-load diesel engines, and the like. Also, automatic transmission fluids, transaxle lubricants, gear lubricants, metal-working lubricants, hydraulic fluids, and other lubricating oil and grease compositions can benefit from the incorporation of the subject additive concentrates.

Natural oils include animal oils and vegetable oils (e.g., castor oil, lard oil) as well as mineral lubricating oils such as liquid petroleum oils and solvent-treated or acid-treated mineral lubricating oils of the paraffinic, naphthenic or mixed paraffinicnaphthenic types. Oils of lubricating viscosity derived from coal or shale are also useful. Synthetic lubricating oils include hydrocarbon oils and halosubstituted hydrocarbon oils such as polymerized and interpolymerized olefins (e.g., polybutylenes, polypropylenes, propyleneisobutylene copolymers, chlorinated polybutylenes, etc.); poly(1-hexenes), poly(1-octenes), poly(1-decenes), etc. and mixtures thereof; alkylbenzenes (e.g., dodecylbenzenes, tetradecylbenzenes, dinonylbenzenes, di-(2-ethylhexyl)-benzenes, etc.); polyphenyls (e.g., biphenyls, terphenyls, alkylated polyphenyls, etc.); alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc., constitute another class of known synthetic lubricating oils that can be used. These are exemplified by the oils prepared through polymerization of ethylene oxide or propylene oxide, the alkyl and aryl ethers of these polyoxyalkylene polymers (e.g., methylpolyisopropylene glycol ether having an average molecular weight of about 1000, diphenyl ether of polyethylene glycol a molecular weight of about 500–1000, diethyl having ether of polypropylene glycol having a molecular weight of about 1000–1500, etc.) or mono- and polycarboxylic esters thereof, for example, the acetic acid esters, mixed $C_3$–$C_8$ fatty acid esters, or the $C_{13}$Oxo acid diester of tetraethylene glycol.

Another suitable class of synthetic lubricating oils that can be used comprises the esters of dicarboxylic acids (e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.) Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also inlcude those made from $C_5$ to $C_{12}$ monocarboxylic acids and polyols and polyol ethers such as neopentyl glycol, trimethylol propane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another useful class of synthetic lubricants (e.g., tetraethyl silicate, tetraisopropyl silicate, tetra-(2-ethylhexyl)silicate, tetra-(4-methylhexyl)silicate, tetra-(p-tert-butyl-phenyl)silicate, hexyl-(4-methyl-2-pentoxy)disiloxane, poly(methyl) siloxanes, poly(methylphenyl)siloxanes, etc.). Other synthetic lubricating oils include liquid esters of phosphorus-containing acids (e.g., tricresyl phosphate, trioctyl phosphate, diethyl ester of decane phosphonic acid, etc.), polymeric tetrahydrofurans and the like.

Unrefined, refined and rerefined oils, either natural or synthetic (as well as mixtures of two or more of any of these) of the type disclosed hereinabove can be used in the concentrates of the present invention. Unrefined oils are those obtained directly from a natural or synthetic source without further purification treatment. For example, a shale oil obtained directly from retorting operations, a petroleum oil obtained directly from primary distillation or ester oil obtained directly from an esterification process and used without further treatment would be an unrefined oil. Refined oils are similar to the unrefined oils except they have been further treated in one or more purification steps to improve one or more properties. Many such purification techniques are known to those skilled in the art such as solvent extraction, secondary distillation, acid or base extraction, filtration, percolation, etc. Rerefined oils are obtained by processes similar to those used to obtain refined oils applied to refined oils which have been already used in service. Such rerefined oils are also known as reclaimed or reprocessed oils and often are additionally processed by techniques directed to removal of spent additives and oil breakdown products.

Generally the lubricants of the present invention contain an amount of one or more of the transition metal salts of this invention sufficient to provide them with improved properties. Normally the amount employed will be about 0.01% to about 20%, preferably about 0.1% to about 10% of the total weight of the lubricating composition. This amount is exclusive of solvent/diluent medium. In lubricating compositions operated under extremely adverse conditions, such as lubricating compositions for marine diesel engines, the transition metal salts of this invention may be present in amounts of up to about 30% by weight, or more, of the total weight of the lubricating composition.

The invention also contemplates the use of other additives in combination with the transition metal salts of this invention. Such additives include, for example, detergents and dispersants of the ash-producing or ashless type, corrosion- and oxidation-inhibiting agents, pour point depressing agents, extreme pressure agents, antiwear agents, color stabilizers and anti-foam agents.

The ash-producing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature of about 50° C. and filtering the resulting mass. The use of a "promoter" in the neutralization step to aid the incorporation of a large excess of metal likewise is known. Examples of compounds useful as the promoter include phenolic substances such as phenol, naphthol, alkylphenol, thiophenol, sulfurized alkylphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenyl-beta-naphthylamine, and dodecylamine. A particularly effective method for preparing the basic salts comprises mixing an acid with an excess of a basic alkaline earth metal neutralizing agent and at least one alcohol promoter, and carbonating the mixture at an elevated temperature such as 60°–200° C.

Ashless detergents and dispersants are so called despite the fact that, depending on its constitution, the dispersant may upon combustion yield a non-volatile material such as boric oxide or phosphorus pentoxide; however, it does not ordinarily contain metal and therefore does not yield a metal-containing ash on combustion. Many types are known in the art, and any of them are suitable for use in the lubricant compositions of this invention. The following are illustrative:

(1) Reaction products of carboxylic acids (or derivatives thereof) containing at least about 34 and preferably at least about 54 carbon atoms with nitrogen containing compounds such as amine, organic hydroxy compounds such as phenols and alcohols, and/or basic inorganic materials. Examples of these "carboxylic dispersants" are described in British Patent No. 1,306,529 and in many U.S. patents including the following:

| | | |
|---|---|---|
| 3,163,603 | 3,399,141 | 3,574,101 |
| 3,219,666 | 3,444,170 | 3,632,510 |
| 3,281,357 | 3,451,933 | 3,697,428 |
| 3,316,177 | 3,501,405 | 3,725,441 |
| 3,346,493 | 3,543,678 | 4,234,435 |

(2) Reaction products of relatively high molecular weight aliphatic or alicyclic halides with amines, preferably olyalkylene polyamines. These may be characterized as "amine dispersants" and examples thereof are described for example, in the following U.S. patents:

| | |
|---|---|
| 3,275,554 | 3,454,555 |
| 3,438,757 | 3,565,804 |

(3) Reaction product of alkyl phenols in which the alkyl group contains at least about 30 carbon atoms with aldehydes (especially formaldehyde) and amines (especially polyalkylene polyamines), which may be characterized as "Mannich dispersants". The materials described in the following U.S. patents are illustrative:

| |
|---|
| 2,459,112 |
| 3,036,003 |
| 3,355,270 |
| 3,442,808 |
| 3,459,661 |
| 3,539,633 |
| 3,591,598 |
| 3,649,229 |
| 3,980,569 |

(4) Products obtained by post-treating the carboxylic, amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. patents:

| | |
|---|---|
| 3,036,003 | 3,493,520 |
| 3,216,936 | 3,533,945 |
| 3,278,550 | 3,579,450 |
| 3,282,955 | 3,639,242 |
| 3,367,943 | 3,658,836 |
| 3,442,808 | 3,708,422 |

(5) Interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. These may be characterized as "polymeric dispersants" and examples thereof are disclosed in the following U.S. patents:

| | |
|---|---|
| 3,329,658 | 3,666,730 |
| 3,519,565 | 3,702,300 |

The above-noted patents are incorporated herein for their disclosures of ashless dispersants.

Extreme pressure agents and corrosion- and oxidation-inhibiting agents which may be included in the lubricants of the invention are exemplified by chlorinated aliphatic hydrocarbons such as chlorinated wax; organic sulfides and polysulfides such as benzyl disulfide, bis(chlorobenzyl)disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate, phosphorus esters including principally dihydrocarbon and trihydrocarbon phosphites such as dibutyl phosphite, diheptyl phosphite, dicyclohexyl phosphite, pentylphenyl phosphite, dipentylphenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl-substituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di(heptylphenyl)phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

Many of the above-mentioned extreme pressure agents and corrosion-oxidation inhibitors also serve as antiwear agents. Zinc dialkylphosphorodithioates are a well known example.

Pour point depressants are a particularly useful type of additive often included in the lubricating oils described herein. The use of such pour point depressants in oil-based compositions to improve low temperature properties of oil-based compositions is well known in the art. See, for example, page 8 of "Lubricant Additives" by C. V. Smalheer and R. Kennedy Smith (Lezius-Hiles Co. publishers, Cleveland, Ohio, 1967).

Examples of useful pour point depressants are polymethacrylates; polyacrylates; polyacrylamides; condensation products of haloparaffin waxes and aromatic compounds; vinyl carboxylate polymers; and terpolymers of dialkylfumarates, vinyl esters of fatty acids and alkyl vinyl ethers. Pour point depressants useful for the purposes of this invention, techniques for their preparation and their uses are described in U.S. Pat. Nos. 2,387,501; 2,015,748; 2,655,479; 1,815,022; 2,191,498; 2,666,746; 2,721,877; 2,721,878; and 3,250,715 which are hereby incorporated by reference for their relevant disclosures.

Anti-foam agents are used to reduce or prevent the formation of stable foam. Typical anti-foam agents include silicones or organic polymers. Additional anti-foam compositions are described in "Foam Control Agents", by Henty T. Kerner (Noyes Data Corporation, 1976), pages 125–162.

The transition metal salts of this invention can be added directly to the lubricant. Preferably, however, they are diluted with a substantially inert, normally liquid organic diluent such as mineral oil, naphtha, benzene, toluene or xylene, to form an additive concentrate. These concentrates usually contain from about 20% to about 90% by weight of the transition metal salts of this invention and may contain, in addition, one or more other additives known in the art or described hereinabove. The remainder of the concentrate is the substantially inert normally liquid diluent.

The following examples illustrate the lubricant compositions of the invention (including additive concentrates).

|  | Wt. % |
|---|---|
| Concentrate A | |
| Solvent-refined, neutral SAE 10 mineral oil | 50 |
| Product of Example 1 | 50 |
| Lubricant A | |
| Mineral oil | 98.5 |
| Product of Example 1 | 1.5 |
| Lubricant B | |
| Synthetic lubricant ($C_{5-9}$ normal alcohol esters of 50/50 molar mixture of adipic and glutaric acids) | 97.5 |
| Product of Example 3 | 2.5 |
| Lubricant C | |
| Mineral oil of Lubricant A | 95.0 |
| Product of Example 3 | 2.5 |
| Tricresyl phosphate | 2.5 |

The fuel compositions containing the transition metal salts of the present invention contain a major proportion of a normally liquid fuel, usually a hydrocarbonaceous petroleum distillate fuel such as motor gasoline as defined by ASTM Specification D439 and diesel fuel or fuel oil as defined by ASTM Specification D396. Normally liquid fuel compositions comprising non-hydrocarbonaceous materials such as alcohols, ethers, organo-nitro compounds and the like (e.g., methanol, ethanol, diethyl ether, methyl ethyl ether, nitromethane) are also within the scope of this invention as are liquid fuels derived from vegetable or mineral sources such as corn, alfalfa, shale and coal. Normally liquid fuels which are mixtures of one or more hydrocarbonaceous fuels and one or more non-hydrocarbonaceous materials are also contemplated. Examples of such mixtures are combinations of gasoline and ethanol and of diesel fuel and ether. Particularly preferred is gasoline, that is, a mixture of hydrocarbons having an ASTM distillation range from about 60° C. at the 10% distillation point to about 205° C. at the 90% distillation point.

Generally, these fuel compositions contain a property improving amount of the transition metal salt compositions of this invention; usually this amount is about 1 to about 50,000 parts by weight, preferably about 4 to about 5000 parts, of the composition of this invention per million parts of fuel.

The fuel compositions can contain, in addition to the composition of this invention, other additives which are well known to those of skill in the art. These include antiknock agents such as tetraalkyl lead compounds, lead scavengers such as haloalkanes (e.g., ethylene dichloride and ethylene dibromide), deposit preventers or modifiers such as triaryl phosphates, dyes, cetane improvers, antioxidants such as 2,6-di-tertiarybuty-4-methyl-phenol, rust inhibitors such as alkylated succinic acids and anhydrides, bacteriostatic agents, gum inhibitors, metal deactivators, demulsifiers, upper cylinder lubricants and anti-icing agents.

In certain preferred fuel compositions the compositions of this invention are combined with an ashless dispersant in gasoline. Suitable ashless dispersants include esters of mono- or polyols and high molecular weight mono- or polycarboxylic acid acylating agents containing at least 30 carbon atoms in the acyl moiety. Such esters are well known to those skilled in the art. See, for example, French Patent No. 1,396,645; British Pat. Nos. 981,850; 1,055,337; and 1,306,529; and U.S. Pat. Nos. 3,255,108; 3,311,558; 3,331,776; 3,346,354; 3,522,179; 3,579,450; 3,542,680; 3,381,022; 3,639,242; 3,697,428; and 3,708,522. These patents are expressly incorporated herein by reference for their disclosure of suitable esters and methods for their preparation. Generally, the weight ratio of the composition of this invention to the aforesaid ashless dispersant is between about 0.1:1 and about 10:1, preferably between about 1:1 and about 10:1.

The transition metal salt compositions of this invention can be added directly to the fuel, or they can be diluted with a substantially inert, normally liquid organic diluent such as naphtha, benzene, toluene, xylene or a normally liquid fuel as described above, to form an additive concentrate. These concentrates generally contain from about 20% to about 90% by weight of the composition of this invention and may contain, in addition one or more other conventional additives known in the art or described hereinabove.

The following examples illustrate the fuel compositions of the invention.

Fuel A

Gasoline having a Reid vapor pressure of 10.5 psi and containing 100 parts per million parts of gasoline of the product of Example 1.

Fuel B

A diesel fuel containing 200 parts per million parts of fuel of the product of Example 1.

Fuel C

Fuel A also containing 2.5 grams per gallon of tetraethyl lead.

The transition metal salt compositions of this invention are useful as additives for paint formulations comprising pigments and vehicle as well as pigment extenders and pigment suspending agents which generally are considered as part of the pigment. Binders, thinners, driers, as well as other optional ingredients such as anti-skin, and anti-slip agents generally are considered in the art as part of the vehicle. The paints to which the transition metal salts of the present invention can be added can be of the primer, enameled, glossy, semi-glossy or flat type. Examples of suitable pigments for the paint formulations include the inorganic and organic types well known in the art such as red lead, red iron oxide, white lead, zinc oxide, zinc chromate, titanium dioxide, lithopone, carbon black, and prussian blue.

Examples of pigment extenders which can be utilized include calcium carbonate, magnesium silicate, silica, aluminum silicate, asbestine, talc, barytes, gypsum, clay or chalk. Exemplary pigment suspending agents include aluminum stearate and zinc stearate.

Binders which can be employed in paints include the vegetable oils such as linseed, both boiled and raw, soybean, tung oil, synthetic polyester-type oils such as glycerine, erythritol or pentaerythritol esters of fatty acids or phthalic and their anhydrides, phenolic resins and alkyl alkyd solids. Examples of suitable thinners include mineral spirits (boiling point 150–215° C.), turpentine and petroleum naphtha. Optional driers which can be utilized include the naphthenates, oxides, resinates, oleates and acetates of cobalt, manganese, lead and zinc. The preferred driers are the naphthenates of cobalt, manganese and lead.

Paint formulations containing the transition metal salts of the invention can be prepared by methods well known in the art. For example, the pigment and vehicle of the paint can be mixed followed by the addition of the transition metal salts of the invention and other optional additives. Alternatively, the vehicle and transition metal salt can be mixed followed by the addition of pigment and other optional ingredients.

The transition metal salt compositions of the present invention function primarily as driers, and, therefore, an amount which is effective to provide the desired drying characteristics of the paint is the amount normally included in the paint formulation. Accordingly, the amount of transition metal salt incorporated into the paint formulation can range from as little as 0.01% to about 5 to 10%. Generally, however, the paint formulation will contain less than 2% by weight of the transition metal salt.

The transition metal salt compositions of the present invention also are useful for reducing the drying time of ink formulations. Ink formulations also are generally comprised of a pigment and a vehicle, and other optional ingredients to alter and improve the properties of the ink formulation. The nature of the vehicle selected will be determined by the properties desired including the properties desired of the dried ink formulation. Examples of vehicles which can be utilized in inks include paraffinic hydrocarbons such as mineral oil, mineral wax, polyethylene, etc., synthetic, polymeric vehicles such as alkyd resins and oil modified alkyd resins. Examples of pigments which can be utilized include polyvalent metal compounds such as lead oxide, nickel carbonate, copper hydroxide, and basic lead carbonate. Examples of suitable thinners include mineral spirits, terpentine and petroleum naphtha. Other optional ingredients which can be included in the ink formulations include anti skinning and anti-slipping agents.

The amount of transition metal salt compositions of the present invention included in the ink formulations of the invention will be an amount which is effective to reduce the drying time of said ink. Generally, the amount of transition metal salt included in the ink will range from about 0.1 to about 5% by weight, but the amount most often will be less than 2% by weight of the ink formulation.

The transition metal salts prepared in accordance with the process of the present invention also are useful as accelerators in the curing of unsaturated polyester resin compositions. The unsaturated polyester resin compositions which can be accelerated with the transition metal salts of the present invention are solutions of unsaturated polyester resins and a polymerizable monomer which provides cross-linking units to unite the polymer chains. The polyester and monomer copolymerize upon the introduction of a catalyst such as a peroxide catalyst to form a rigid, insoluble, infusable material. The unsaturated polyester resin compositions are used in the production of coatings, laminates, cast articles, molded articles, and other shaped articles.

Accelerators are usually added to unsaturated polyester resin compositions to accelerate the decomposition of the peroxide catalyst to free radicals and thereby initiate or speed up the curing of the composition at relatively low temperatures, i.e., at temperatures in the range of $-30°$ C. to $+30°$ C. The transition metal salts of the present invention, particularly, the vanadium salts, are especially effective accelerators, and can be used alone, or in combination with other known accelerators such as cobalt, manganese, iron, and aluminum salts of organic acids; amines such as dimethyl aniline, diethyl aniline, and 2-aminopyridene; Lewis acids, such as boron fluoride dihydrate, and ferric chloride; bases such as tetraethyl ammonium hydroxide and tetramethyl ammonium hydroxide, etc. Cobalt salts of organic acids are the most widely used accelerators for the low temperature decomposition of peroxide catalysts and in the curing of unsaturated polyester resin compositions.

The polyester resins that are used in the practice of this invention are unsaturated polyester resins that are formed by condensing an unsaturated polycarboxylic acid or anhydride with at least one polyhydric alcohol. Illustrative of these polyester resins are the products of the reaction of a saturated dicarboxylic acids or anhydride, such as phthalic anhydride, isophthalic acid, tetrahydrophthalic anhydride, hexahydrophthalic anhydride, tetrachlorophthalic anhydride, hexachloroendomethylene tetrahydrophthalic acid, succinic acid, glutaric acid, adipic acid, pimelic acid, suberic acid, azelaic acid, and sebacic acid, and an unsaturated dicarboxylic acid or anhydride, such as maleic anhydride, fumaric acid, chloromaleic acid, itaconic acid, citraconic acid, and mesaconic acid, with a dihydric alcohol, such as ethylene glycol, propylene glycol, butylene glycol, diethylene glycol, triethylene glycol, and neopentyl glycol. Small amounts of a polyhydric alcohol, such as glycerol, pentaerythritol, trimethylolpropane, or sorbitol, may be used in combination with the glycol.

A three-dimensional structure is produced by reacting the unsaturated polyester through the unsaturated acid component with an unsaturated monomer that is capable of reacting with the polyester resin to form cross-linkages. Suitable unsaturated monomers include styrene, methylstyrene, dimethylstyrene, vinyltoluene, divinylbenzene, dichlorostyrene, methyl acrylate, ethyl acrylate, methyl methacrylate, ethyl methacrylate diallyl phthalate, vinyl acetate, triallyl cyanurate, acrylonitrile, acrylamide, and mixtures thereof. The relative amounts of the unsaturated polyester resin and the unsaturated monomer in the composition may be varied over a wide range. In order to prevent gelation during manufacture and storage, the polyester resin may be stabilized as known in the art. Some examples of well-known stabilizers include hydroquinone, quinone, tertiary butyl catechol, etc.

The unsaturated polyester resin compositions generally contain 20% to 80% by weight of the monomer, with the monomer content preferably in the range of 30% to 70% by weight.

When it is desired to copolymerize the unsaturated polyesters with the vinyl monomer to form a useful solid product, some source of free radicals is added. The free radicals cause copolymerization of the monomer and polyester to yield a cross-linked material whose properties are dependent on the original choice of dicarboxylic acids, polyhydric alcohols, and liquid monomers. Typical free radical producing catalysts include the various redox systems, high-energy electron beams, and a variety of peroxide compounds.

An organic peroxide that decomposes to release free radicals at temperatures in the range of 0° 30° C. generally is used to catalyze the copolymerization reaction between the unsaturated polyester resin and the unsaturated monomer. Among the peroxide catalysts that can be used are methyl ethyl ketone peroxide, benzoyl peroxide, cumene hydroperoxide, cetyl peroxide, lauroyl peroxide, cyclohexanone peroxide, 2,4-dichlorobenzoyl peroxide, bis(p-bromobenzoyl)peroxide, acetyl peroxide, and di-tert-butyl diperphthalate. The peroxide catalysts that are most commonly used are methyl ethyl ketone peroxide, benzoyl peroxide, and cumene hydroperoxide. The amount of peroxide catalyst used is from 0.1% to 2.0% and preferably from 0.6% to 1.0% of the weight of the unsaturated polyester resin composition.

The amount of the transition metal salt of the invention included in the polyester resin formulation is an amount which is effective to accelerate the decomposition of the peroxide and to reduce the drying (or get time) of the resin formulation. Generally, the amount of accelerator will be sufficient to provide from about 0.0001 to 1.0% of transition metal (as metal). More typically the range will be about 0.001 to about 0.1%. When more than one accelerator is used, the total amount of metal will fall wtthin this range. For example, the transition metal salts of the invention can be used in combination with other metal salts normally used as accelerators for polyester resins. Such salts include cobalt, manganese, iron, and aluminum salts prepared by methods known to those skilled in the art.

In addition to the unsaturated polyester resin, cross-linking monomer, peroxide catalyst, and one of the accelerator systems of this invention, the unsaturated polyester resin compositions may also contain an inhibitor, such as tert, butyl-catechol or hydroquinone, fillers and pigments, dyes, mold release agents, plasticizers, stabilizers, flame-retardants, and other additives in the amounts ordinarily used for these purposes.

The unsaturated polyester resin compositions that comprise an unsaturated polyester resin, an unsaturated monomer, a peroxide catalyst, and a transition metal salt accelerator system cure rapidly without application of heat to form rigid, insoluble, and infusible products.

The utility of the transition metal salts of the invention as accelerators for polyester resins is illustrated as follows. A commercially available Cargill GP Marble Resin formulation is prepared containing cumene hydroperoxide and 0.24 parts per 100 parts of polyester resin of the vanadium salt of Example 1. The gel time for this formulation is significantly less than a similar formulation containing no accelerator or a cobalt salt accelerator.

I claim:

1. A process for preparing hydrocarbon-soluble transition metal salt composition of organic carboxylic acids having improved properties wherein the transition metal is one capable of having a multiplicity of oxidation states comprising the steps of
    (a) providing at least one transition metal compound wherein the transition metal is at one of its higher positive oxidation states,
    (b) reducing said transition metal compound with at least one hydrazine source forming an intermediate containing the transition metal in a lower positive oxidation state, and
    (c) reacting said intermediate with at least one organic carboxylic acid containing at least 5 carbon atoms to form the transition metal salt of said carboxylic acid.

2. The process of claim 1 wherein the transition metal compound of (a) is an oxide of vanadium, molybdenum, tungsten or rhenium.

3. The process of claim 1 wherein the hydrazine source is hydrazine, semicarbazides, a hydrazine dicarboxylate of a lower alkanol, a mixture of two or more of these, or mixtures of one or more of these with water.

4. The process of claim 3, wherein the reducing agent is hydrazine.

5. The process of claim 1 wherein the organic carboxylic acid includes at least one aliphatic or alicyclic monocarboxylic acid containing from about 6 to about 30 carbon atoms.

6. The process of claim 1 wherein the transition metal is vanadium or molybdenum.

7. The process of claim 1 wherein step (b) is conducted in the presence of an effective amount of at least one promoter.

8. The process of claim 7 wherein the promoter is ammonia, an ammonium halide, or an organic nitrogen compound.

9. The process of claim 1 wherein the mole ratio of transition metal compound to reducing agent is from about 1:0.1 to 1:5.

10. The process of claim 1 wherein step (b) is conducted at a temperature of from about room temperature up to about 85° C.

11. The process of claim 1 wherein step (c) is conducted at a temperature of from about room temperature to about 200° C.

12. The process of claim 1 conducted at about atmospheric pressure.

13. A process for preparing hydrocarbon-soluble vanadium and molybdenum salts of organic carboxylic acids having improved properties which comprises the steps of
 (a) providing at least one vanadium or molybdenum oxide compound wherein the vanadium and molybdenum are at one of their higher positive oxidation states,
 (b) reducing said vanadium or molybdenum oxide compound with at least one hydrazine source to form an intermediate containing the vanadium or molybdenum in a lower positive oxidation state, and
 (c) reacting said intermediate with at least one aliphatic or alicyclic carboxylic acid containing from about 6 to about 30 carbon atoms to form the vanadium or molybdenum salt of said carboxylic acid.

14. The process of claim 13 wherein the hydrazine source is hydrazine, semicarbazides, a hydrazine dicarboxylate of a lower alkanol, a mixture of two or more of these, or mixtures of one or more of these with water.

15. The process of claim 13 wherein the carboxylic acid includes at least one aliphatic or alicyclic monocarboxylic acid containing from about 8 to about 10 carbon atoms.

16. The process of claim 13 wherein step (b) is conducted in the presence of an effective amount of at least one promoter.

17. The process of claim 16 wherein the promoter is ammonia, an ammonium halide, or an organic nitrogen compound.

* * * * *